United States Patent [19]

Asano et al.

[11] Patent Number: 4,750,140

[45] Date of Patent: Jun. 7, 1988

[54] METHOD OF AND APPARATUS FOR DETERMINING GLOSSINESS OF SURFACE OF A BODY

[75] Inventors: Yuichiro Asano, Palo Alto, Calif.; Motoji Shiozumi, Kobe; Hitoshi Aizawa, Kurashiki; Yoshiaki Shibata, Chiba, all of Japan

[73] Assignee: Kawasaki Steel Corporation, Hyogo, Japan

[21] Appl. No.: 802,742

[22] Filed: Nov. 29, 1985

[30] Foreign Application Priority Data

Nov. 30, 1984 [JP] Japan ................................ 59-253529
Nov. 30, 1984 [JP] Japan ................................ 59-253530
Nov. 27, 1985 [JP] Japan ................................ 60-266638

[51] Int. Cl.$^4$ ............................................. G01N 21/55
[52] U.S. Cl. ..................................... 364/526; 356/445
[58] Field of Search ............... 364/525, 526, 472, 473, 364/; 356/445–448, 371; 350/6.5, 6.1

[56] References Cited

U.S. PATENT DOCUMENTS 4,124,803 11/1978 Bowers ................................ 250/559
4,408,880 10/1983 Tsuji et al. ........................... 364/525
4,585,343 4/1986 Schave et al. ....................... 356/445

FOREIGN PATENT DOCUMENTS 60-97204 5/1985 Japan .
2123139A 1/1984 United Kingdom .

OTHER PUBLICATIONS

Eckerle et al., "NBS Reference Retroreflectometer", Applied Optics, vol. 19, No. 8, pp. 1253–1259, Apr. 15, 1980.
DE-U-1 944 088 (Farbenfabriken Bayer AG) FIG. 1; p. 3, line 10–p. 4, line 19, 08/11/1966.
WO-A-8 400 213 (Labsystems OY) abstract p. 3, line 20–p. 4, line 22, 06/29/1982.
P. Beckmann et al. "The Scattering of Electromagnetic Waves from Rough Surfaces", chapters 3 and 5.
"Tetsu-to-Hagane (Iron & Steel)", vol. 70 (1984) pp. 1095–1102.

Primary Examiner—Parshotam S. Lall
Assistant Examiner—Brian M. Mattson
Attorney, Agent, or Firm—Parkhurst & Oliff

[57] ABSTRACT

A method and apparatus classifies and grades glossiness based on the visible feeling by the light reflection intensity distribution of a surface of a body, wherein specular reflection intensities and total reflection intensities are detected for two known light fluxes projected at predetermined incident angles. The specular reflection intensities and the total reflection intensities are processed, to thereby determine the glossiness of the work to be measured.

11 Claims, 10 Drawing Sheets

METHOD OF AND APPARATUS FOR DETERMINING GLOSSINESS OF SURFACE OF A BODY

BACKGROUND OF THE INVENTION

This invention relates to a method of and an apparatus for determining the glossiness of a surface of a body, and more particularly to improvements in a method of and an apparatus for determining the glossiness of a surface of a body, suitable for use in measuring the surface quality of a steel sheet to control the same, wherein the glossiness based on visible feeling is classified and graded in accordance with the light reflection intensity distribution of the surface of the body.

Various methods of determining the glossiness of a surface of a body have heretofore been proposed which utilize light reflection measurement.

Such methods include:

(1) a method of measuring by specular surface glossiness, wherein the specular reflection intensity of a white light flux projected at a predetermined angle is measured;

(2) a method of measuring by contrasting glossiness, wherein a ratio between the main reflection intensity and the scattered reflection intensity of a white light projected at a predetermined angle is used; and (3) a method of measuring by sharp glossiness, wherein another body is reflected by a surface and a blurred shape of the reflected image is visually inspected.

The method of measuring by specular surface glossiness is widely used in industry, but is inaccurate where the specular surface object has a low surface roughness. Furthermore, the method of measuring by contrasting glossiness is accurate for objects which are different in color from one another, but is less accurate with objects having nearly a specular surface. Further, the method of measuring by sharp glossiness is disadvantageous since no quantitative indication can be obtained.

SUMMARY OF THE INVENTION

The present invention has been developed to obviate the disadvantages of the prior art and has as its object the provision of a method of and an apparatus for determining glossiness of a surface of a body, wherein, with objects which are identical in color with one another (which may be different in luminosity from one another), the result of measurement coincide with the visible glossiness and the glossiness can be determined quantitatively over a wide range of roughness degrees from the specular surface to the rough surface.

Figure 1:
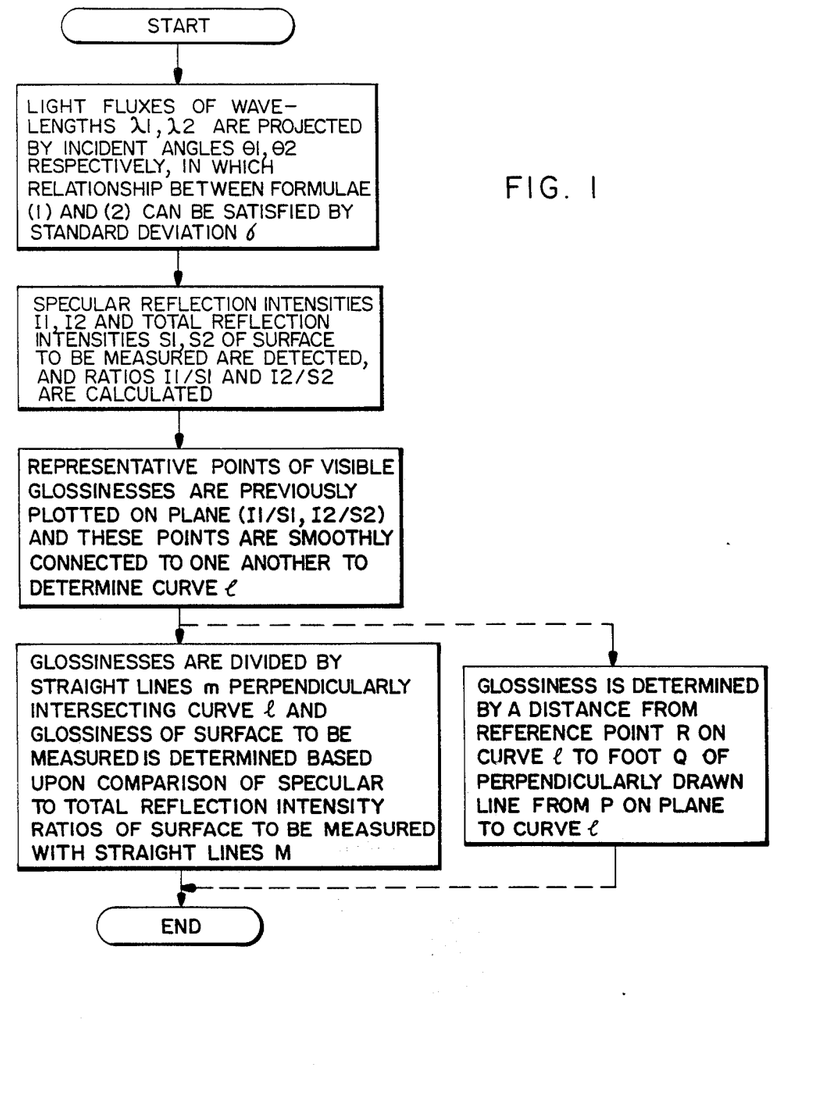
FIGS. 1 and 2 are flow charts showing the gists of the methods of determining glossiness of the surface of a body according to the present invention.

To this end, the present invention contemplates that, in a method of determining glossiness of a surface of a body, wherein the glossiness based on the visible feeling is classified and graded in accordance with a light reflection intensity distribution of the surface of the body, as the gist thereof is shown in FIG. 1, light fluxes having wavelengths $\lambda_1$ and $\lambda_2$, by which a standard deviation $\sigma$ of the height distribution of a profile of a surface to be measured satisfies the relationship between the following formulae, are projected at incident angles $\theta_1$ and $\theta_2$, respectively, $$(4\pi\sigma/\lambda_1 \cdot \cos\theta_1)^2 \leq 1 \qquad (1)$$

$$(4\pi\sigma/\lambda_2 \cdot \cos\theta_2)^2 \geq 4 \qquad (2)$$

specular reflection intensities I1 and I2 and total reflection intensities S1 and S2 are detected, representative points of respective visible glossiness are previously plotted on a two dimensional plane (I1/S1, I2/S2) and the representative points are smoothly connected to one another to determine a curve 1, and the glossiness of a work to be measured are determined by straight lines m perpendicularly intersecting the curve 1.

A specific form of the present invention is of such an arrangement that centroid points of the respective visible glossiness are selected as the representative points, so that adequate representative points can be easily obtained.

Another specific form of the present invention is of such an arrangement that the curve 1 is determined by constructing a drawing so that an adequate curve 1 can be easily obtained.

A further specific form of the present invention is of such an arrangement that the straight lines m are obtained by plotting a multiplicity of sample points, whereby the number of points turned to be mistakenly determined can be minimized for the adjoining groups, so that an adequate straight line m can be easily obtained.

As indicated by broken lines in FIG. 1, so the above end, the present invention further contemplates that, that, the glossiness of a work to be measured is evaluated by a distance from a reference point R on the curve 1 along the cuve 1 to a foot Q of a perpendicularly drawn line from a point P on the two dimensional plane of the work to be measured to the curve 1.

A still further specific form of the present invention is of such an arrangement that the glossiness of an arbitrary point on the curve 1 is determined to be a proportionally interpolated value along the curve 1 in each of the sections, and the glossiness of an arbitrary sample is made to be the glossiness of a point at which is positioned a foot Q of a perpendicularly drawn line from a point P associated with the sample on the two dimensional plane to the curve 1, so that the glossiness of the arbitrary sample to be measured can be quantitatively obtained.

Figure 2:
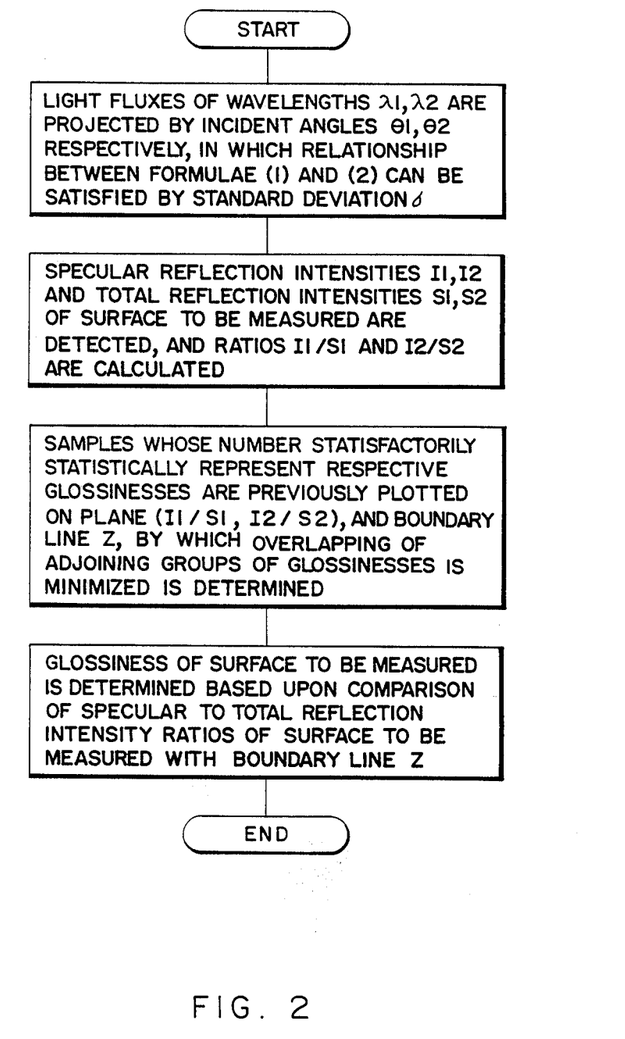

To the above end, a further embodiment of the present invention contemplates that, in a method of determining the glossiness of a surface of a body, wherein the golssiness based on the visible feeling is classified and graded in accordance with the light reflection intensity distribution of the surface of the body, as the gist thereof is shown in FIG. 2, light fluxes having wavelengths $\lambda_1$ and $\lambda_2$, by which a standard deviation $\sigma$ of a height distribution of a profile of a surface to be measured satisfies the relationship between the above-mentioned formulae (1) and (2), are projected at incident angles $\theta_1$ and $\theta_2$, respectively, respective specular reflection intensities I1 and I2 and total reflection intensities S1 and S2 are detected, samples, whose number satisfactorily statistically represents the respective visible glossiness, are previously plotted on a two dimensional plane (I1/S1, I2/S2), with a plurality of groups glossiness being present on the two dimensional plane, a boundary line Z as being a discriminant function, by which the overlapping of respective adjoining groups of glossiness comes to be the minimum, is determined, and the glossiness of an arbitrary work to be measured is divided by the boundary line Z.

A yet further specific form of the present invention is of such an arrangement that the boundary line Z is determined such that, when two dimensional distributions of adjoining groups are projected on an axis Zv normal to the boundary line Z, the overlapping formed thereby is minimized, so that an adequate boundary line Z can be easily obtained.

Figure 3:
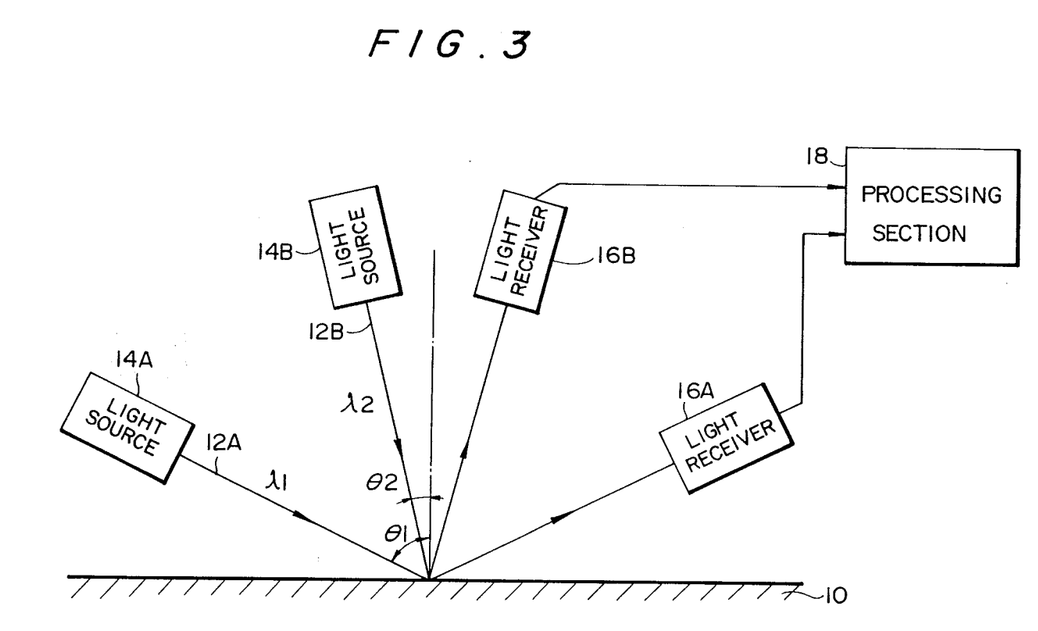
FIG. 3 is a block diagram showing the gist of the arrangement of the apparatus for determining the glossiness of the surface of a body according to the present invention.

To the above end, further, the present invention contemplates that, in an apparatus for determining glossiness of a surface of a body, wherein the glossiness based on the visible feeling is classified and graded in accordance with the light reflection intensity distribution of the surface of the body, as the gist of arrangement thereof is shown in FIG. 3, the apparatus comprises:

two light sources 14A and 14B, which project light fluxes 12A and 12B having wavelengths λ1 and λ2, by which a standard deviation σ of a height distribution of the profile of a surface to be measured satisfies the relationship between the above-mentioned formulae (1) and (2), at incident angles θ1 and θ2, respectively;

two light receivers 16A and 16B for detecting respective specular reflection intensities I1 and I2 and respective total reflection intensities S1 and S2; and a processing section 18 for processing the specular reflection intensities I1, I2 and the total reflection intensities S1, S2 to thereby determine the glossiness of a work 10 to be measured.

A specific form of the present invention is of such an arrangement that the light receivers comprise photodiodes arranged in a two dimensional array form, so that the specular and total reflection intensities can be detected easily without movable parts.

Another specific form of the present invention is of such an arrangement that the light receiver has an aperture provided in front thereof and the opening area of the aperture is made variable, so that the specular and total reflection intensities can be detected easily.

The present invention is based on the fact that the visible glossiness of a surface of a body such as a steel sheet is a function of two surface roughness degrees, including the average roughness and the average interval between crests, and evaluation cannot be performed based only upon the average roughness.

More specifically, surface roughness is the main factor in determining the glossiness of objects having colors substantially identical with each other, and it is basically considered that, when information of the surface roughness is accurately grasped, the glossiness can be accurately evaluated.

Generally speaking, the information of the surface roughness can be expressed by the standard deviation σ of the height distribution of the profile of the surface to be measured and an auto-correlation distance T (a distance, where an auto-correlation function becomes 1/e). This value and the light reflection intensity distribution have a predetermined relationship as shown in "The Scattering of Electromagnetic Waves from Rough Surfaces" under a joint authorship of P. Beckmann and A. Sprizzichino, published by Pergamon Press in 1963.

Further, according to the results of a detailed study made by Yuichiro Asano et al on this relationship, which is published in "TETSU-TO-HAGANE (IRON & STEEL), Vol. 70 (1984)", page 1095 and forth, when the scope of the formulae (1) and (2) are satisfied, the specular reflection intensities I1 and I2 have the relationships shown in the following equations with the parameters of the roughness degree σ and T:

$$I1 = f1(\sigma) \quad (3)$$

$$I2 = f2(\sigma, T) \quad (4)$$

where the incident light intensity is a unit intensity and the total reflection factor is 1.

When taking into account the total reflection factor, the left side of the above-mentioned equations (3) and (4) are replaced by I1/S1, I2/S2 (S1 and S2 are the total reflection intensities under the conditions of the formulae (1) and (2)), respectively, and the information of the parameters of the roughness degree σ and T is reliably included in the both I1/S1 and I2/S2. As a consequence, the glossinesses are determined by both of I1/S1 and I2/S2, and can be determined quantitatively.

Figure 4:
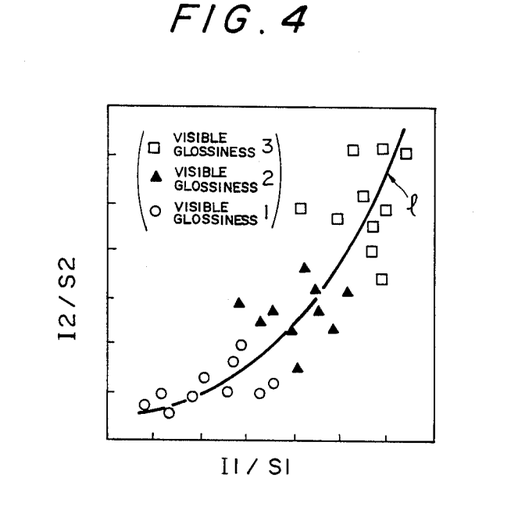
FIG. 4 is a chart showing an example of the state of distribution of the samples on a two dimensional plane (I1/S1, I2/S2) in explanation of the principle of the first method according to the present invention.

On the other hand, when consideration is given to a multiplicity of samples having the qualities of types identical with one another, but being different in visible glossiness from one another, if these samples are plotted on a two dimensional plane (I1/S1, I2/S2), as shown in FIG. 4 for example, there are many cases where these samples are continuously distributed along the predetermined curve 1 on the two dimensional plane according to the glossiness thereof. In FIG. 4, designated at ○ is a sample having the visible glossiness 1, ● a sample having the visible glossiness 2 and □ a sample having the visible glossiness 3, respectively.

Figure 5:
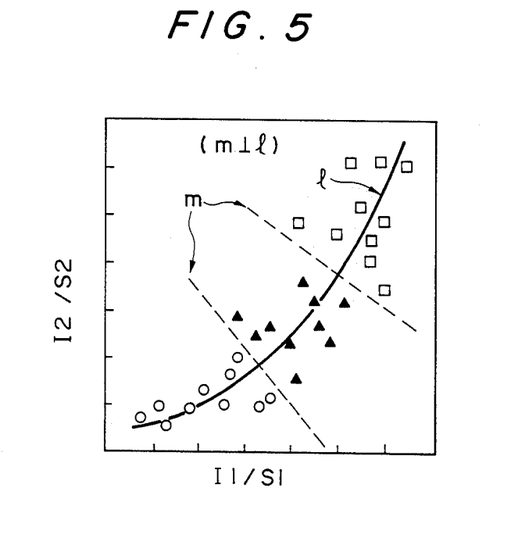
FIG. 5 is a chart showing an example of the curve 1 and straight lines m on the two dimensional plane (I1/S1, I2/S2) in explanation of the principle of the first method.
Figure 6:
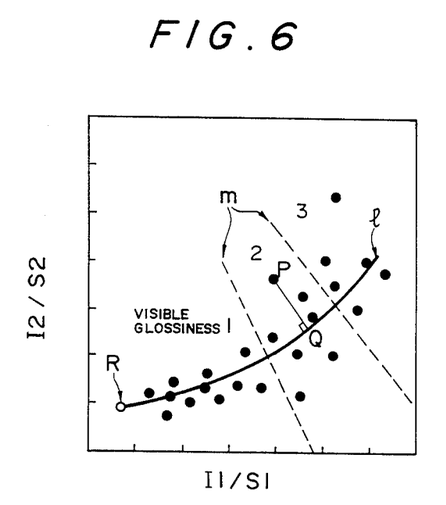
FIG. 6 is a chart showing the simplest example wherein the sample points are classified by the first method according to the present invention.
Figure 7:
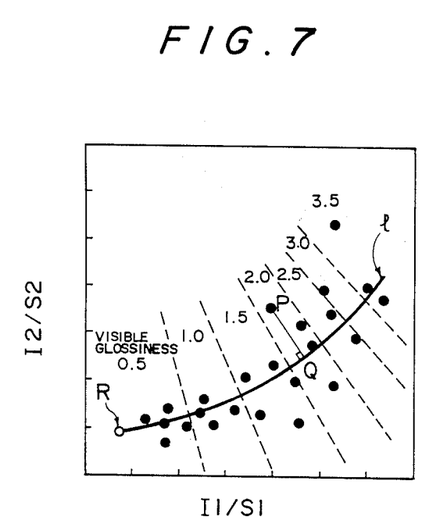
FIG. 7 is a chart showing an example wherein the visible glossiness are further finely evaluated by the first method according to the present invention.

Consequently, when the glossiness of these samples are classified on the two dimensional plane (I1/S1, I2/S2), the first method of FIG. 5 of classifying the glossiness by straight lines m normal to the curve 1 is adequate and simple. Alternatively, representative points of the respective visible glossiness are plotted on the two dimensional plane (I1/S1, I2/S2), and a curve 1 obtained by smoothly connecting these points is determined by construction on a drawing, for example. Subsequently, the glossiness of an arbitrary sample to be measured is evaluated by determining a distance (or a value equivalent thereto) from a reference point R on the curve 1 along the curve 1 to a foot Q of a perpendicularly drawn line from a point P of the sample on the two dimensional plane. FIG. 6 shows the simplest example wherein the sample points are classified in accordance with the visible glossiness 1, 2 and 3. FIG. 7 shows an example wherein these visible glossiness are more finely evaluated.

Figure 8:
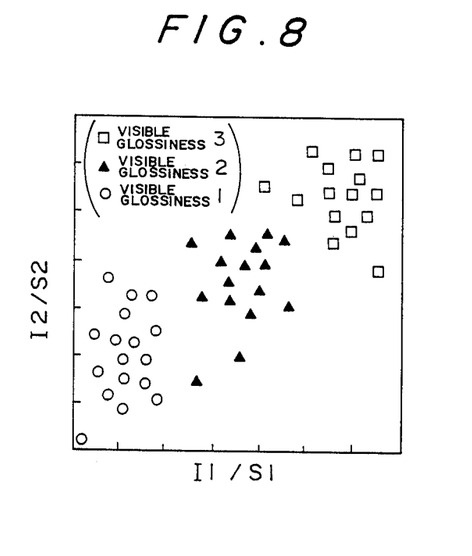
FIG. 8 is a chart showing an example of the state of distribution of the samples on the two dimensional plane (I1/S1, I2/S2) in explanation of the principle of the second method according to the present invention.

As another alternative, a multiplicity of samples having the qualities of types identical with one another, but being different in visible glossiness from one another are plotted on a two dimensional plane (I1/S1, I2/S2). As shown in FIG. 8 for example, there are many cases where these samples are distributed on the two dimensional plane in a plurality of groups in accordance with the glossiness thereof. In FIG. 8, designated at ○ is a sample having the visible glossiness 1, ● a sample having the visible glossiness 2 and □ a sample having the visible glossiness 3, respectively.

Figure 9:
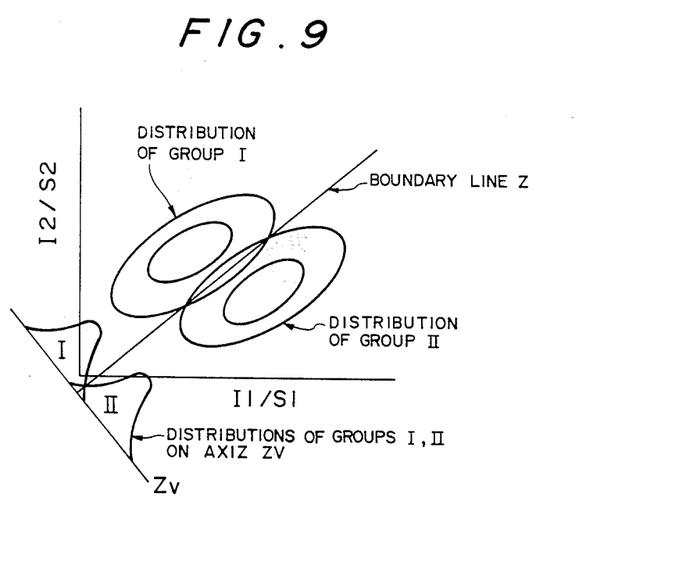
FIG. 9 is a chart showing an example of the method of dividing the groups of glossiness in explanation of the principle of the second method.

When the glossiness of these samples are divided on the two dimensional plane (I1/S1, I2/S2), as a second method, such a method is adequate that the boundary line Z is determined such that the overlap between the respective adjoining groups of samples is statiscally minimized, thereby dividing the samples. The boundary line Z for minimizing the statistical overlap between the two adjoining groups is derived by use of a discriminant function. As shown in FIG. 9 for example, this boundary line Z can be determined such that, when the two dimensional distributions of the adjoining groups are projected onto an axis Zv normal to the boundary line Z, the overlap at the projections of the adjoining groups is minimized. According to this second method, a boundary line Z12 between the glossiness 1 and 2 and a boundary line Z23 between the glossiness 2 and 3 of the groups of glossiness as shown in FIG. 8 are determined, and the divided state is shown in FIG. 10.

Figure 10:
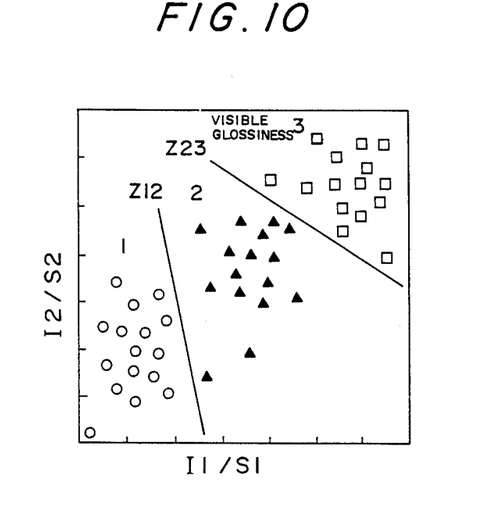
FIG. 10 is a chart showing an example wherein the groups of glossiness are divided by the second method according to the present invention.

For example, the boundary line Z23 between the glossiness 2 and 3 as shown in an example of FIG. 10 is determined as shown below. More specifically, when data shown in Table 1 is obtained on the respective glossiness, the following statistics are calculated by the following equations:

$$\overline{Xi^{(1)}} = \sum_{a=1}^{n} Xai^{(1)}/n \tag{5}$$

$$\overline{Xi^{(2)}} = \sum_{b=1}^{m} Xbi^{(2)}/m \tag{6}$$

$$\overline{Xi} = (\overline{Xi^{(1)}} + \overline{Xi^{(2)}})/2 \tag{7}$$

$$di = \overline{Xi^{(1)}} - \overline{Xi^{(2)}} \ (i = 1, 2, \ldots p) \tag{8}$$

$$Sij = \sum_{a=1}^{n} (Xai^{(1)} - \overline{Xi^{(1)}})(Xaj^{(1)} - \overline{Xj^{(1)}}) + \tag{9}$$

$$\sum_{b=1}^{m} (Xbi^{(2)} - \overline{Xi^{(2)}})(Xbj^{(2)} - \overline{Xj^{(2)}})(i, j = 1, 2, \ldots p)$$

$$Vij = Sij/(n + m - 2) \tag{10}$$

TABLE 1

| CHARACTERISTIC VALUE | | $I_1/S_1$ | $I_2/S_2$ |
|---|---|---|---|
| GLOSSINESS 3 | 1 | $X_{11}^{(1)}$ | $X_{12}^{(1)}$ |
|  | 2 | $X_{21}^{(1)}$ |  |
|  | 3 | $X_{31}^{(1)}$ |  |
|  | . | . | . |
|  | a | $X_{a1}^{(1)}$ | $X_{a2}^{(1)}$ |
|  | . | . | . |
|  | n | $X_{n1}^{(1)}$ | $X_{n2}^{(1)}$ |
|  | AVERAGE | $\overline{X_1^{(1)}}$ | $\overline{X_2^{(1)}}$ |
| GLOSSINESS 2 | 1 | $X_{11}^{(2)}$ | $X_{12}^{(2)}$ |
|  | 2 | $X_{21}^{(2)}$ |  |
|  | 3 | $X_{31}^{(2)}$ |  |
|  | . | . | . |
|  | b | $X_{b1}^{(2)}$ | $X_{b2}^{(2)}$ |
|  | . | . | . |
|  | m | $X_{m1}^{(2)}$ | $X_{m2}^{(2)}$ |
|  | AVERAGE | $\overline{X_1^{(2)}}$ | $\overline{X_2^{(2)}}$ |

Here, the equations (5) and (6) calculate mean values, equation (9) calculates the sum of the squares and the sum of the products, and the equation (10) calculates the variance and covariance.

The boundary line Z, as a the discriminant function, can be determined from the above-mentioned statistics through the following equations:

$$Z = \sum_{i=1}^{p} ai(Xi - \overline{Xi}) \tag{11}$$

$$ai = \sum_{i=1}^{p} Vij \cdot dj \tag{12}$$

$$\therefore a = V^{-1} d \tag{13}$$

The foregoing describes the method of determining the discriminant function having two parameters. According to this method of determining the discriminant function, a discriminant function having more than two parameters can be determined as well.

In using the first or the second method, as shown in FIG. 3, the glossiness of the surface of the work 10 to be measured can be determined in such a manner that the light fluxes 12A and 12B are projected to the surface of the work 10 to be measured from the two light sources 14A and 14B having the wavelengths λ1 and λ2 and the incident angles θ1 and θ2 which satisfy the conditions of the above-mentioned formulae (1) and (2), the specular reflection intensities I1, I2 and the total reflection intensities S1, S2 are detected by the light receivers 16A and 16B, and the specular reflection intensities I1, I2 and the total reflection intensities S1, S2 are adequately processed by the processing section 18 in accordance with the first or the second method.

Figure 11:
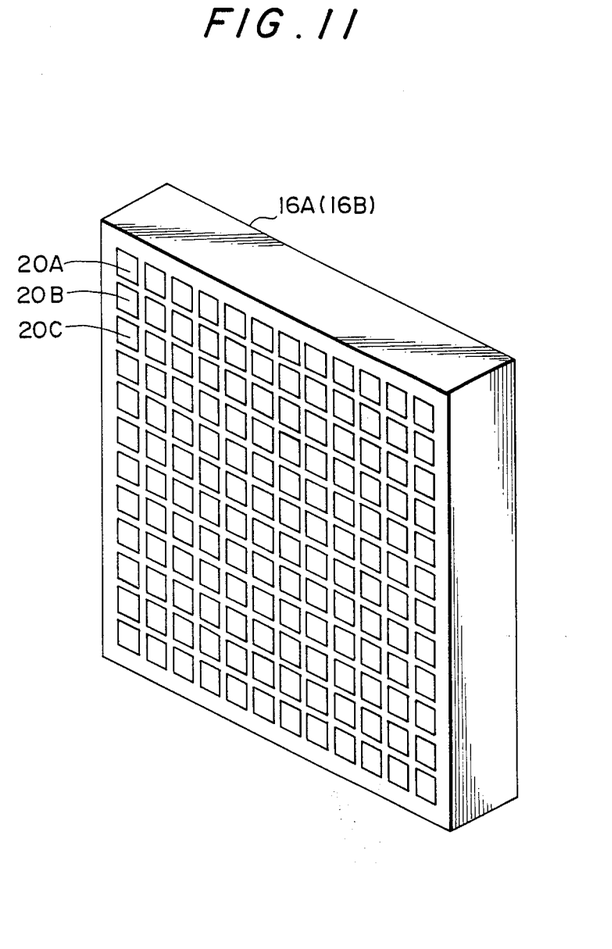
FIG. 11 is a perspective view showing an example of the arrangement of the light receiver used in the apparatus according to the present invention.
Figure 12:
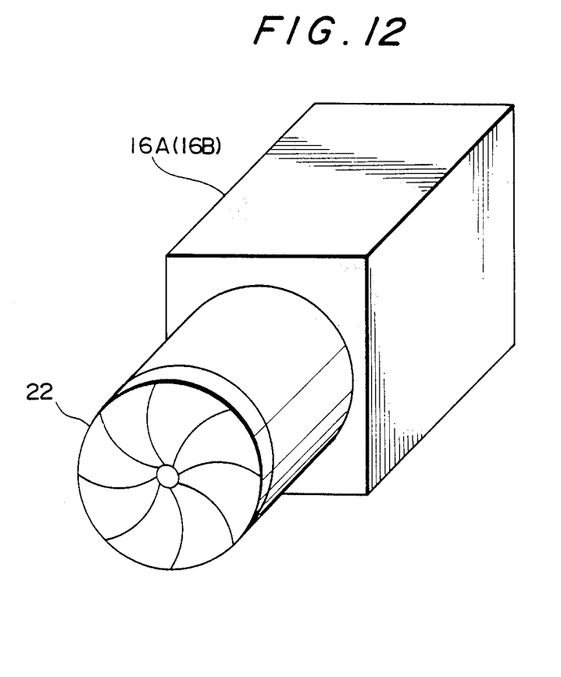
FIG. 12 is a perspective view showing another example of the arrangement of the light receiver used in the apparatus according to the present invention.

The light receiver 16A (16B) for detecting the specular reflection intensity I1 (I2) and the total reflection intensity S1 (S2), as shown in FIG. 11 for example, may be a group of photodiodes 20A, 20B, 20C . . . arranged in a two dimensional array form, from which the quantity of detected light of the specific photodiode which is on the specular reflecting direction becomes the specular reflection intensity I1 (I2) and the total sum of the entire light received becomes the total reflection intensity S1 (S2). The expansion (area) of the two dimensional array of the photodiodes 20A, 20B, 20C . . . should have the expansion (area) sufficient for receiving the total reflection light to insure accurate determination of S1 (S2). Or, as shown in FIG. 12, the light receiver 16a (16B) may have an aperture 22 provided in front of the light receiver 16A (16B) rendering the opening area of the aperture 22 variable, so that the specular reflection intensities I1 (I2) and the total reflection intensities S1 (S2) can be detected.

According to the present invention, with the objects having colors identical with one another (although the louminosity may differ), a glossiness may be determined which coincides with the visible glossiness and a wide range of roughness (from the specular surface to the rough surface) can be quantitatively measured. It thus becomes possible to accurately measure and control the surface qualities on-line, so that outstanding practical advantages such as the prevention of the occurrence of defects results.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein.

DESCRIPTION OF THE PREFERRED EMBODIMENTS

Detailed description will hereunder be given of an example of the first embodiment wherein the evaluation of the glossiness of a stainless steel sheet is made in accordance with the first method of the first embodiment of the present invention.

This first example is provided to test the performance of the automatic determination method as a replacement for the determination of glossiness under the conventional visual inspection (four grades of the glossiness 1 to 4) by the automatic determination through the measurement of the light reflection intensities I1 and I2.

A parameter $\sigma$ of the surface roughness of the stainless steel sheet, which is treated here, is 0.02 to 0.2 micrometer. If an Ar laser beam of $\lambda = 0.457$ micrometer is utilized as the light flux, then the above-mentioned formula (1) can be satisfied by an incident angle $\theta = 75°$, and the above-mentioned formula (2) can be satisfied at an incident angle $\sigma = 10°$. In the case of the stainless steel sheet which is treated here, the total reflection factors are substantially constant, and the two dimensional plane (I1/S1, I2/S2) used in the evaluation of the glossiness is equivalent to (I1, I2).

Figure 13:
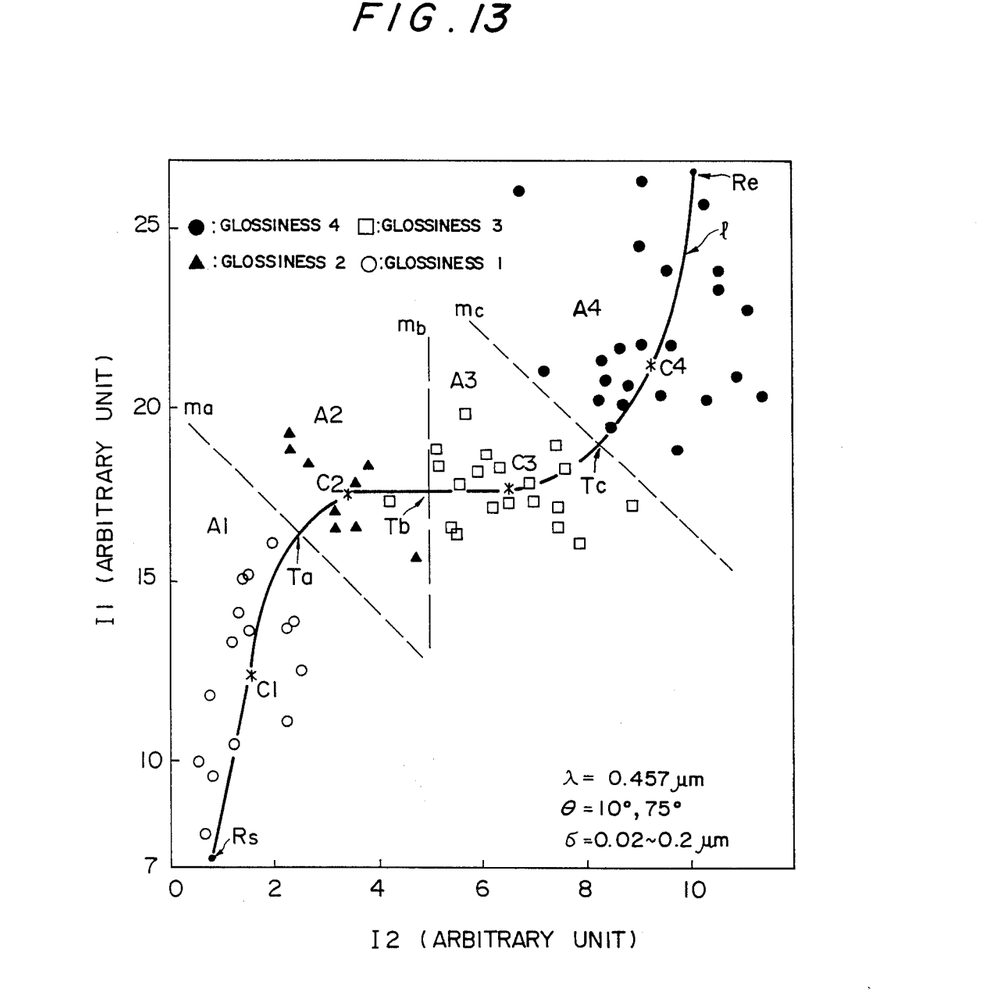
FIG. 13 is a chart showing the result of determination of a first embodiment, wherein the evaluation of the glossiness of a stainless steel sheet is made under the application of the first method according to the present invention.

FIG. 13 shows the result of determination by this first embodiment. The respective samples are classified into four grades of the glossiness 1 to 4 through the visual inspection made by a plurality of skilled inspectors by comparing the samples with the reference samples. In FIG. 13, ○, ▲, □ and ● indicate the samples having the glossinesses 1, 2, 3 and 4, respectively.

With these samples, the specular reflection intensities I1 and I2 were measured, and, for the samples belonging to the respective glossiness, representative points (centroid points in this first embodiment) C1 to C4 on the two dimensional plane of (I1, I2) were determined. Thereafter, these points were smoothly connected to one another on the plane to draw the curve 1. Subsequently, adequate boundary lines ma, mb and mc which perpendicularly intersect the curve 1, respectively, were determined so that the samples to be measured can be classified by respective glossiness. As the practical method of determining these boundary lines ma, mb and mc, for example, a multiplicity of sample points are plotted and the boundary lines ma, mb and mc are determined so that the number of points which are mistakenly determined is minimized for the respective adjoining groups.

As the result of automatically determining a multiplicity of stainless steel sheets by the determining method sought through the above-mentioned steps, about 97% of the samples were accurately determined, thereby demonstrating the satisfactory performance of the determining method.

Alternatively, as a method of determining the glossiness more finely, the glossiness at the respective representative points C1, C2, C3 and C4 are set at 1.0, 2.0, 3.0 and 4.0, the glossiness of reference point Rs, a point of intersection Ta between the curve 1 and the boundary line ma, a point of intersection Tb between the curve 1 and the boundary line mb, a point of intersection Tc between the curve 1 and the boundary line mc, and the reference points are made to be 0.5, 1.5, 2.5, 3.5 and 4.5, respectively, and further, the glossiness of arbitrary points on the curve 1 are to be proportionally interpolated values along the curve 1 in respective sections (0.5 to 1.0, 1.0 to 1.5 ... 4.0 to 4.5), so that the glossiness of each of the arbitrary samples to be measured is determined to be the glossiness of a point positioned at the foot Q of a perpendicularly drawn line from the point P associated with the sample on the two dimensional plane of (I1, I2) to the curve 1.

The analog determination of glossiness can be performed by this alternative method.

Detailed description will hereunder be given of the second embodiment wherein the determination of the glossiness of a cold-rolled steel sheet is performed by the second method according to the present invention.

This second method is also provided to test the performance of the automatic determination as a replacement for the determination of the glossiness under the conventional visual inspection (four grades of the glossiness 1 to 4) by the automatic determination through the measurement of the light reflection intensities I1 and I2.

The parameter $\sigma$ of the surface roughness of the cold-rolled steel sheet treated here is 0.1 to 0.5 micrometer. When a He-Na laser beam having a wavelength of $\lambda = 0.633$ micrometer is utilized as the light flux, the formula (1) can be satisfied by an incident angle $\theta = 75°$ and the formula (2) can be satisfied by an incident angle $\theta = 10°$. Furthermore, in the case of the cold-rolled steel sheet treated here, the total reflection factor is substantially constant, and the two dimensional plane (I1/S1, I2/S2) used for the evaluation of the glossiness is equivalent in value to the two dimensional plate (I1, I2).

Figure 14:
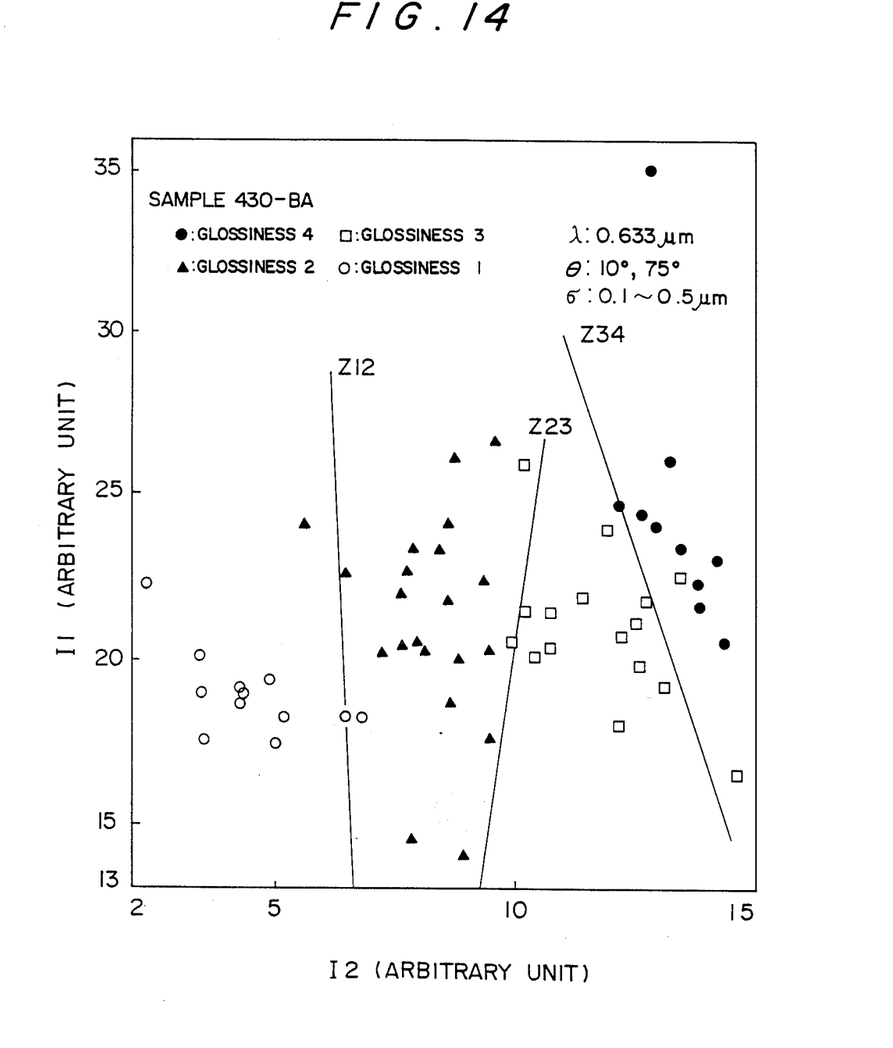
FIG. 14 is a chart showing the result of determination of a second embodiment, wherein the determination of the glossiness of a cold-rolled steel sheet is made under the application of the second method according to the present invention.

FIG. 14 shows the result of determination by the second embodiment. The respective samples were classified into four grades of glossiness 1 to 4 through the visual inspection made by a plurality of skilled inspectors by comparing the samples with the reference samples. in FIG. 14, ○, ▲, □ and ● indicate the samples having the glossiness 1, 2, 3 and 4, respectively.

On the other hand, with these samples, the specular reflection intensities I1 and I2 were measured, and, with the samples belonging to the respective glossiness, boundary lines Z34, Z23 and Z12 as being the discriminant functions were derived between the respective groups of glossiness on the two dimensional plane I1, I2). The boundary lines Z34, Z23 and Z12 thus derived were represented by the following equations.

$$Z34 = 0.0043\ (I2-1278) + 0.0029\ (I1-2269) \quad (14)$$

$$Z23 = 0.0219\ (I2-1017) - 0.0035\ (I1-2113) \quad (15)$$

$$Z12 = 0.03\ (I2-642) = 0.0007\ (I1-2011) \quad (16)$$

The glossiness of a multiplicity of samples of the cold-rolled steel sheet were determined by use of the boundary lines Z34, Z23 and Z12 thus determined. As a result, the determination of glossiness of about 90% of the samples was accurately performed, whereby the method was ascertained to have a satisfactory determining capacity.

In the above-described embodiments, the present invention has been applied to the evaluation and determination of the glossiness of stainless steel and cold-rolled steel sheets, however, the scope of application of the present invention need not necessarily be limited to this, and it is apparent that the present invention is applicable to the determination of glossiness of the surface of an ordinary body.

What is claimed is:

1. A method of determining glossiness of a surface to be measured, wherein the glossiness based on visible feeling is classified and graded in accordance with a light reflection intensity distribution of said surface to be measured, comprising the steps of:

(a) presetting wavelengths $\lambda 1$, $\lambda 2$ and incident angles $\theta 1$, $\theta 2$ of first and second light fluxes, respectively, such that $\lambda 1$, $\lambda 2$, $\theta 1$, $\theta 2$ and a standard deviation $\sigma$ of a height distribution of a profile of said surface satisfy the following relationships:

$$(4\pi\sigma/\lambda 1.\cos\theta 1)^2 \leq 1$$

$$(4\pi\sigma/\lambda 2.\cos\theta 2)^2 \geq 4$$

(b) predetermining for a sample of representative surfaces of known varying glossiness specular reflection intensities I1, I2 and total reflection intensities S1, S2 from said first and second light fluxes, respectively;

(c) plotting representative points corresponding to I1/S1 and I2/S2 on a two dimensional plane for said representative surfaces, smoothly fitting a curve 1 to such plotted points, and storing such curve in a processing section;

(d) projecting said first and second light fluxes having wavelengths $\lambda 1$ and $\lambda 2$, respectively, upon said surface to be measured at said incident angles $\theta 1$ and $\theta 2$, respectively;

(e) detecting, for said first and second light fluxes, respectively, specular reflection intensities I1 and I2 and total reflection intensities S1 and S2 of said surface to be measured; and (f) determining in said processing section the glossiness of the surface to be measured by plotting a point corresponding to I1/S1 and I2/S2 for said surface to be measured on said two dimensional plane and comparing said plotted point to at least one straight line m perpendicularly intersecting said curve 1.

2. The method as set forth in claim 1, wherein said plotted representative points are centroid points of sample points of the representative surfaces.

3. The method as set forth in claim 1, wherein said curve 1 is determined by construction on a drawing.

4. The method as set forth in claim 1, wherein said at least one straight line m is determined by plotting sample points of the representative surfaces and minimizing the number of such sample points for adjoining groups which would be mistakenly determined in view of the determination of said at least one line m.

5. A method of determining glossiness of a surface to be measured, wherein the glossiness based on visible feeling is classified and graded in accordance with a light reflection intensity distribution of said surface to be measured, comprising the steps of:

(a) presetting wavelengths $\lambda 1$, $\lambda 2$ and incident angles $\theta 1$, $\theta 2$ of first and second light fluxes, respectively, such that $\lambda 1$, $\lambda 2$, $\theta 1$, $\theta 2$ and a standard deviation of a height distribution of a profile of said surface satisfy the following relationships:

$$(4\pi\sigma/\lambda 1.\cos\theta 1)^2 \leq 1$$

$$(4\pi\sigma/\lambda 2.\cos\theta 2)^2 \geq 4$$

(b) predetermining for a sample of representative surfaces of known varying glossiness specular reflection intensities I1, I2 and total reflection intensities S1, S2 from said first and second light fluxes, respectively;

(c) plotting representative points I1/S1 and I2/S2 on a two dimensional plane for said representative surfaces, smoothly fitting a curve 1 to such plotted points, and storing such curve in a processing section;

(d) projecting said first and second light fluxes having wavelengths $\lambda 1$ and $\lambda 2$, respectively, upon said surface to be measured at said incident angles $\theta 1$ and $\theta 2$, respectively;

(e) detecting, for said first and second light fluxes, respectively, specular reflection intensities I1 and I2 and total reflection intensities S1 and S2 of said surface to be measured; and (f) determining in said processing section the glossiness of the surface to be measured by plotting a point P corresponding to I1/S1 and I2/S2 for said surface to be measured on said two dimensional plane and determining a distance along said curve 1 from a reference point R on said curve 1 to a foot Q of a perpendicularly drawn line from said point P to said curve 1.

6. A method as set forth in claim 5, wherein the glossiness of an arbitrary point on said curve 1 is determined to be a proportionally interpolated value along said curve 1, and the glossiness of said surface to be measured is determined to be the glossiness of a point at which is positioned a foot Q of a perpendicularly drawn line from point P to said curve 1.

7. A method of determining glossiness of a surface to be measured, wherein the glossiness based on visible feeling is classified and graded in accordance with a light reflection intensity distribution of said surface to be measured, comprising the steps of:

(a) presetting wavelengths $\lambda 1$, $\lambda 2$ and incident angles $\theta 1$, $\theta 2$ of first and second light fluxes, respectively, such that $\lambda 1$, $\lambda 2$, $\theta 1$, $\theta 2$ and a standard deviation $\sigma$ of a height distribution of a profile of said surface satisfy the following relationships:

$$(4\pi\sigma/\lambda 1 . \cos\theta 1)^2 \leq 1$$

$$(4\pi\sigma/\lambda 2 . \cos\theta 2)^2 \geq 4$$

(b) predetermining for a sample of representative surfaces of known varying glossiness specular reflection intensities I1, I2 and total reflection intensities S1, S2 from said first and second light fluxes, respectively;

(c) plotting representative points corresponding to I1/S1 and I2/S2 on a two dimensional plane for said representative surfaces, determining one or more glossiness boundary lines Z using a discriminant function whereby overlapping of representative points of adjoining groups of glossiness are minimized and storing said one or more boundary lines in a processing section;

(d) projecting said first and second light fluxes having wavelengths $\lambda 1$ and $\lambda 2$, respectively, upon said surface to be measured at said incident angles $\theta 1$ and $\theta 2$, respectively;

(e) detecting, for said first and second light fluxes, respectively, specular reflection intensities I1 and I2 and total reflection intensities S1 and S2 of said surface to be measured; and (f) determining in said processing section the glossiness of the surface to be measured by plotting a point corresponding to I1/S1 and I2/S2 for said surface to be measured on said two dimensional plane and determining where said point is located with respect to said one or more boundaries Z.

8. The method as set forth in claim 7, wherein said one or more boundary lines Z are determined such that an overlap of plotted projections of adjoining groups of glossiness on an axis Zv normal to said respective boundary line Z is minimized.

9. An apparatus for determining glossiness of a surface to be measured, wherein the glossiness based on visible feeling is classified and graded in accordance with a light reflection intensity distribution of said surface to be measured, said apparatus comprising:

first and second light sources having wavelengths $\lambda 1$ and $\lambda 2$, positioned to project light fluxes upon said surface to be measured at incident angles $\theta 1$ and $\theta 2$, respectively, such that a standard deviation $\sigma$ of a height distribution of a profile of said surface to be measured and $\lambda 1$, $\lambda 2$, $\theta 1$ and $\theta 2$ satisfy the following relationship:

$$(4\pi\sigma/\lambda 1 . \cos\theta 1)^2 \leq 1$$

$$(4\pi\sigma/\lambda 2 . \cos\theta 2)^2 \geq 4$$

two light receivers for detecting respective specular reflection intensities I1 and I2 and respective total reflection intensities S1 and S2 of said surface to be measured projected by said first and second light sources, respectively; and processing means for evaluating the glossiness of said surface to be measured based on said detected specular reflection intensities I1 and I2 and said detected total reflection intensities S1 and S2, and utilizing a relationship between the glossiness and ratios of said intensities I1/S1 and I2/S2.

10. An apparatus as set forth in claim 9, wherein at least one of said receivers comprises photodiodes arranged in a two dimensional array form.

11. An apparatus as set forth in claim 9, wherein at least one of said light receivers has an aperture provided in front thereof and an opening area of said aperture is made variable.

* * * * *